Figure 1:
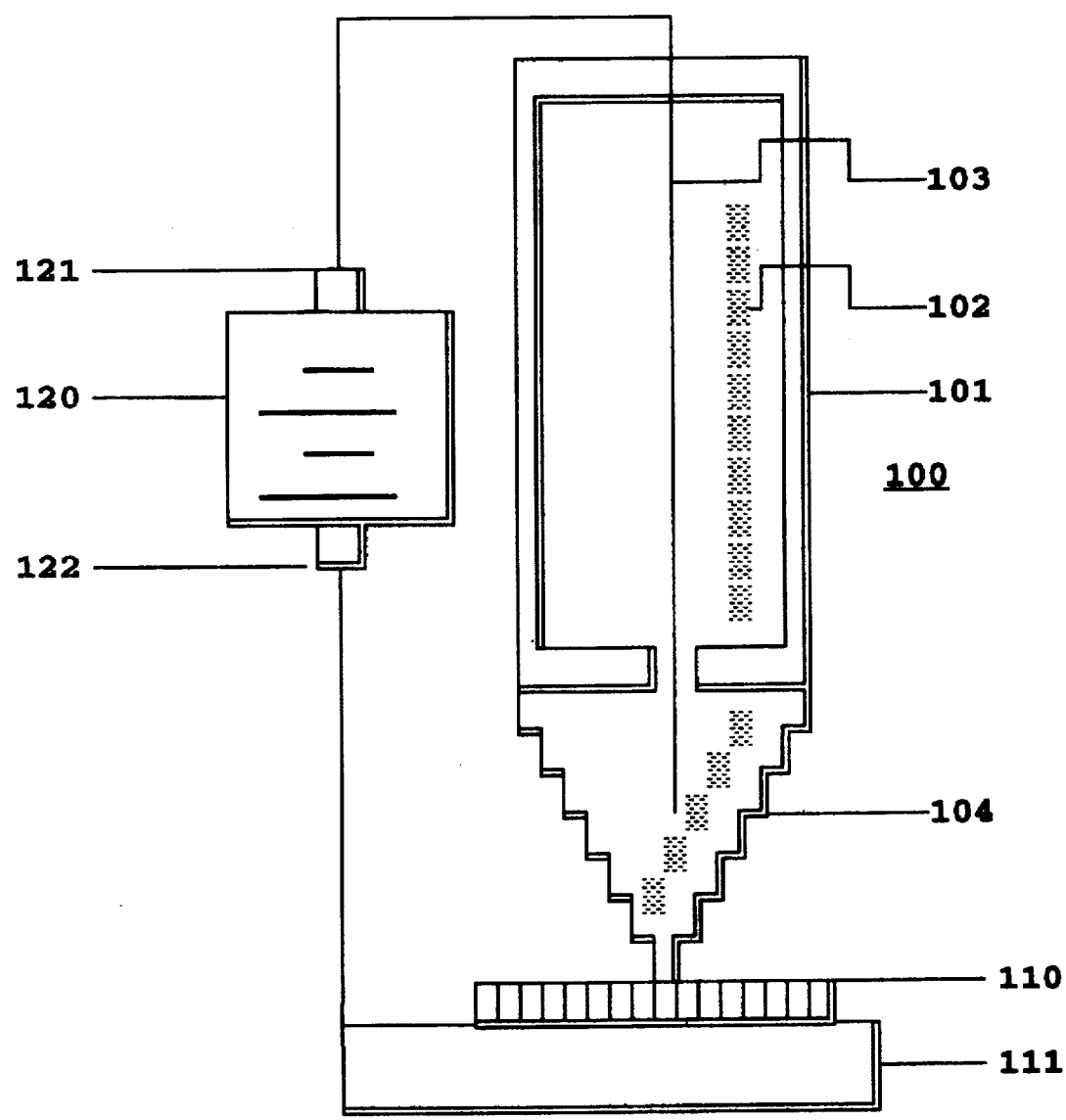

United States Patent [19]
Reiss

[11] Patent Number: 5,716,513
[45] Date of Patent: Feb. 10, 1998

[54] ELECTROGRAPHIC PEN

[76] Inventor: Andre Reiss, 147-47 Village Rd., Jamaica, N.Y. 11435

[21] Appl. No.: 634,519
[22] Filed: Apr. 18, 1996
[51] Int. Cl.$^6$ ..................................... G01N 27/26
[52] U.S. Cl. ................. 205/790; 204/400; 205/775
[58] Field of Search .................. 204/400; 205/775, 205/790, 790.5, 791, 791.5

[56] References Cited

U.S. PATENT DOCUMENTS

| | | |
|---|---|---|
| 2,531,747 | 11/1950 | Stearn. |
| 3,028,317 | 4/1962 | Wilson et al.. |
| 3,236,759 | 2/1966 | Robinson. |
| 3,282,804 | 11/1966 | Stearn. |
| 4,053,381 | 10/1977 | Hamblen et al.. |
| 4,799,999 | 1/1989 | Medvinsky et al.. |
| 4,824,551 | 4/1989 | Rupich. |
| 5,080,766 | 1/1992 | Moment et al. ............ 205/790 |

OTHER PUBLICATIONS

Feigl, "Inorganic Spot Tests", 6th English edition, Elsevier Pub. Co., New York, 1960 month unavailable, pp. 428–429, 56–61.

Lerner, "Detection of Gold in Plating", Industrial and Engineering Chemistry, vol. 15, (1944) month unavailable, p. 416.

Calamari, "Rapid Detection of Gold by the Electrographic Method", Industrial and Engineering Chemistry, vol. 14, (1943) month unavailable, p. 535.

*Primary Examiner*—T. Tung

[57] ABSTRACT

A pen shaped electrochemical cell houses a nib shaped diaphragm dispensing aqueous ammonium bromide charged to a potential of about 3 volts. The device is used to coat an identifying reddish ink comprising gold bromide on a test electrode comprising gold.

5 Claims, 1 Drawing Sheet

ELECTROGRAPHIC PEN

BACKGROUND OF THE INVENTION

The invention relates to an electrochemical test device and method for identifying gold.

Around 1930 Glazunow and Jirkovski described an electrochemical test device for identifying the composition of a metal. Electricity and electrolyte dissolved a metal test electrode into ions visualized by an added colorimetric reagent. This electrographic cell comprised no formal cell housing, but did comprise a battery means coupling a ground electrode and a test electrode across a diaphragm comprising a paper wet with an electrolyte and a colorimetric reagent. A test cell for identifying gold was not disclosed.

In 1943, the U.S. Treasury Department described electrographic identification of gold on a filter paper wet with a fluid mixture of a conductive electrolyte comprising sulfuric acid and a colorimetric reagent comprising tin chloride to generate a purple composition on a paper diaphragm. Two alternative fluid compositions were also described: an electrolyte comprising acetic acid mixed with a reagent comprising benzidine to generate a blue composition; and an electrolyte comprising sodium nitrate mixed with a reagent comprising hydrogen peroxide to generate a red composition. To their disadvantage, these cells required bulky apparatus and complex fluid solutions.

An object of my invention is to disclose a simplified fluid for making gold test devices. A secondary object is to define a portable form for future gold testing devices using this simplified fluid.

BRIEF DESCRIPTION OF THE INVENTION

FIG. 1 shows a cell of the invention.

DESCRIPTION OF THE INVENTION

FIG. 1 illustrates my electrochemical cell device testing a composition comprising gold. A pen assembly 100 comprises a pen barrel 101 containing a nib shaped diaphragm 104 and a wire shaped ground electrode 103 immersed in a fluid 102 carrying a charge from the negative terminal 121 of a battery means 120, through the wire shaped ground electrode 103, through the fluid 102, onto a test electrode 110, comprising the metal to be tested in electrical contact with the positive terminal 122 of the battery means 120; whereupon the test electrode 110 comprising gold is coated with a reddish ink 111.

My pen shaped device comprises an electrochemical half cell fit to a pen assembly. The pen cell comprises: a pen barrel, a ground electrode, a nib, and a fluid; corresponding to the classical cell housing, cathode, diaphragm, and electrolyte. A second test half cell comprises a test metal contacting the fluid dispensed from the nib; corresponding to anode, electrolyte, and diaphragm.

The nib shaped diaphragm comprises porous polypropylene. The wire shaped ground electrode comprises gold or gold plated tungsten wire. The clear fluid comprises a solution of 2 to 16 Molar aqueous bromide ion, and preferably comprises about 6 Molar ammonium bromide because of its high specific conductance of about 220 millimho/cm at 25 deg C, The test electrode comprising metallic gold is visibly reformed by the test device into a peculiar reddish ink in the steps of:

1) electrolysis, in which the battery means charges the conductive fluid to reform the test electrode comprising gold metal into aqueous gold ions;

2) chemical precipitation, in which the test ions comprising gold formed by (1) reform the clear fluid into the reddish ink comprising precipitated gold bromide. The reaction steps are additionally described by:
1) $Au - 3e \rightarrow Au^{+++}$
2) $Au^{+++} + 3Br^- \rightarrow AuBr_3$ The test device dispenses to the test electrode about 10 microliter of the clear fluid carrying about 50 millicoulomb of battery charge per 5 second test period. The fluid carrying 50 millicoulomb of battery charge, preferably comprising 10 milliampere for 5 seconds test time, is sufficient to display an identifying coating on the test electrode.

The ink is only displayed on the test electrode comprising gold. Other metal test electrodes including cadmium, chromium, cobalt, copper, iron, lead, nickel, titanium, palladium, and platinum, silver, tin, and zinc do not display color during wetting contact to the nib shaped diaphragm dispensing 6 Molar aqueous ammonium bromide charged from a battery to a potential of 3 volts.

Embodied in my invention is a simplification over the prior art of building electrographic test devices for identifying gold. A clear fluid comprising a single bromide salt dissolved in water replaces the complex prior mixtures of an electrolyte composition and a reagent composition. In my invention, the single aqueous bromide salt wetting the diaphragm serves both as an electrolyte and as a reagent.

EXAMPLE

A writing fluid is made by mixing, by weight, two parts dry ammonium bromide with three parts water at 40 degrees Centigrade. The clear solution is allowed to cool to room temperature whereupon some solid ammonium bromide crystallizes out. The supernatant fluid comprises about 6 Molar ammonium bromide with a specific conductance of about 220 millimho/cm at 25 deg C.

A pen barrel is constructed to contain the fluid in wet contact to a ground electrode and a diaphragm. The ground electrode is made from gold or gold plated tungsten wire and the diaphragm is made from permeable polypropylene. The device is constructed to expose the ground electrode through the cell housing for permanent electrical contact to the negative terminal (−) of a 3 volt battery means. The positive terminal (+) of the 3 volt battery means is fitted with a clip for removable electrical contact to a test electrode. The device is also constructed to expose the diaphragm in the shape of a nib for dispensing fluid to a metal surface by writing means at a preferable rate of 2 microliter per second.

Writing contact for 5 seconds transfers about 10 microliter of fluid carrying 50 millicoulomb of battery charge from the pen device to the test electrode; whereupon the test electrode surface reforms into a reddish ink coloring the test electrode identifiably.

I claim:

1. A method for identifying gold comprising:
   providing a housing containing an electrode and a clear fluid, said fluid comprising aqueous bromide ions in the range of 2 to 16 Molar;
   dispensing said fluid through a nib shaped diaphragm of the housing to a test electrode comprising gold; and
   connecting a negative terminal of a voltage source to the electrode in the housing and a positive terminal of the voltage source to the test electrode to effect electrolysis and a reddish ink coating on the test electrode.

2. The method of claim 1 where said fluid comprises about 6 Molar ammonium bromide.

3. The method of claim 1 wherein said coating comprises precipitated gold bromide.

4. An electrochemical pen for testing gold comprising:

a housing in the shape of a pen barrel;

a nib shaped diaphragm protruding from a bottom of said barrel;

a wire electrode protruding from a top of said barrel;

a clear fluid electrolyte and reagent within said barrel and adapted to be dispensed to a test electrode comprising gold through said diaphragm, said fluid comprising about 6 Molar aqueous ammonium bromide; and a battery of about 3 volts having its negative terminal connected to the wire electrode and its positive terminal connected to the test electrode.

5. The pen of claim 4 wherein the diaphragm dispenses said fluid to said test electrode in the microliter range to effect an identifying ink coating comprising gold bromide on said test electrode.

* * * * *